(12) United States Patent
Hauger et al.

(10) Patent No.: US 12,125,135 B2
(45) Date of Patent: Oct. 22, 2024

(54) SYSTEM FOR ACQUIRING AND VISUALIZING OCT SIGNALS

(71) Applicant: Carl Zeiss Meditec AG, Jena (DE)

(72) Inventors: Christoph Hauger, Aalen (DE); Tilman Schmoll, Wien (AU); Nancy Hecker-Denschlag, Ulm (DE); Joachim Steffen, Westhausen (DE)

(73) Assignee: CARL ZEISS MEDITEC AG, Jena (DE)

( * ) Notice: Subject to any disclaimer, the term of this patent is extended or adjusted under 35 U.S.C. 154(b) by 0 days.

(21) Appl. No.: 18/363,320

(22) Filed: Aug. 1, 2023

(65) Prior Publication Data

US 2024/0054717 A1     Feb. 15, 2024

(30) Foreign Application Priority Data

Aug. 10, 2022   (DE) ..................... 10 2022 120 203.8

(51) Int. Cl.
| | |
|---|---|
| *G06T 15/08* | (2011.01) |
| *A61B 3/10* | (2006.01) |
| *A61B 5/00* | (2006.01) |
| *A61B 90/00* | (2016.01) |
| *A61B 90/20* | (2016.01) |
| *G06T 15/20* | (2011.01) |

(Continued)

(52) U.S. Cl.
CPC ............ *G06T 15/08* (2013.01); *A61B 5/0066* (2013.01); *A61B 90/20* (2016.02); *G06T 15/20* (2013.01); *H04N 13/117* (2018.05); *H04N 13/207* (2018.05); *H04N 13/398* (2018.05); *A61B 2090/3735* (2016.02); *G06T 2200/24* (2013.01); *G06T 2210/62* (2013.01)

(58) Field of Classification Search
USPC ......................................................... 345/156
See application file for complete search history.

(56) References Cited

U.S. PATENT DOCUMENTS

| | | | |
|---|---|---|---|
| 2008/0024721 A1* | 1/2008 | Ueno ..................... | A61B 3/102 348/78 |
| 2012/0019777 A1 | 1/2012 | Hauger et al. | |

(Continued)

FOREIGN PATENT DOCUMENTS

DE   10 2015 104 560      9/2016

OTHER PUBLICATIONS

European Search Report for App. No. 23183360.9, dated Dec. 18, 2023 (20 pages).

(Continued)

*Primary Examiner* — Chineyere D Wills-Burns
(74) *Attorney, Agent, or Firm* — NIXON PEABODY LLP; Jeffrey L. Costellia (57) ABSTRACT

The present invention relates to a system for acquiring and visualizing OCT signals, comprising an OCT system and a display means designed for the time-resolved display of image data. The system further comprises a control unit configured to drive the OCT system to acquire a time-resolved OCT signal of a selected field of view of the sample and to determine a time-resolved OCT image on the basis of the acquired time-resolved OCT signal and a specifiable virtual viewing direction and to display the time-resolved OCT image on the display means. The present invention also relates to a corresponding method for acquiring and visualizing OCT signals.

16 Claims, 4 Drawing Sheets

(51) Int. Cl.
*H04N 13/117* (2018.01)
*H04N 13/207* (2018.01)
*H04N 13/398* (2018.01)

(56) References Cited

U.S. PATENT DOCUMENTS

| | | |
|---|---|---|
| 2012/0092615 A1 | 4/2012 | Izatt |
| 2015/0094566 A1* | 4/2015 | Ryu ................ A61B 5/489 600/424 |
| 2018/0045927 A1* | 2/2018 | Heeren ................ A61B 3/10 |
| 2019/0183584 A1* | 6/2019 | Schneider ............ A61B 34/20 |
| 2020/0077883 A1* | 3/2020 | Ehlers ................ A61B 3/0025 |
| 2021/0169320 A1 | 6/2021 | Tripathi |
| 2021/0169324 A1* | 6/2021 | Tripathi ............ H04N 13/246 |
| 2021/0267801 A1* | 9/2021 | Akiyama ............ G06T 11/008 |
| 2022/0117696 A1* | 4/2022 | Shi ................ A61B 90/30 |

OTHER PUBLICATIONS

German Office Action for Application No. 10 2022 120 203.8, mailed Apr. 19, 2023 (12 pages).

Li et al., "A practical comparison between Zhang's and Tsai's calibration approaches," In: IVCNZ'14, Proceedings of the 29th International Conference on Image and Vision Computing, Nov. 2014, New Zealand, 2014, pp. 166-171.

Ehlers et al., "Integration of a Spectral Domain Optical Coherence Tomography System into a Surgical Microscope for Intraoperative Imaging," Investigative, Ophthalmology & Visual Science, May 2011, vol. 52, No. 6, pp. 3153-3159.

Draelos et al., "Real-time visualization and interaction with static and live optical coherence tomography volumes in immersive virtual reality," Research Article, vol. 9, No. 6, Jun. 1, 2018, Biomedical Optics Express, pp. 2825-2843.

* cited by examiner

SYSTEM FOR ACQUIRING AND VISUALIZING OCT SIGNALS

CROSS-REFERENCE TO RELATED APPLICATIONS

The present application claims priority under 35 U.S.C. § 119 to German Patent Application No. 10 2022 120 203.8, filed Aug. 10, 2022, the contents of which are incorporated by reference herein in their entirety.

SUBJECT MATTER OF THE INVENTION

The present invention relates to a system for acquiring and visualizing OCT signals, in particular for acquiring time-resolved OCT signals and for visualizing the OCT signals in the form of time-resolved OCT images. The present invention also relates to a method for acquiring and visualizing OCT signals.

TECHNOLOGICAL BACKGROUND

The use of technological aids is part and parcel of modern medicine. By now, imaging methods and robotic systems are used equally as a matter of course in both surgery and diagnostics. In this context, the use of imaging methods allows the display and discrimination of various structures in the patient and the image data obtained from the patient can be used advantageously in diagnostics and also in therapeutic and surgical methods.

By way of example, image data of a patient not only allows a surgeon to plan a surgical intervention better, but also assists them in performing the intervention. Robotic visualization systems are used to assist surgeons when performing surgical interventions. Said systems generally comprise at least one camera for recording images of the region to be operated on, with said camera being carried by a stand with an articulated structure. The stand allows the camera to be positioned relative to the subject by way of translational and/or rotational movements, in order to capture images of a desired field of view (FOV) of the region to be operated on. In this context, the use of optical stereo cameras allows the acquisition of 3-D image data.

In addition to the acquisition of surface information from a desired field of view, for example on the basis of reflected or back-scattered visible light, methods for acquiring depth information from the field of view have also been developed in the meantime. These methods include optical coherence tomography (OCT), which allows the three-dimensional microscopic imaging of optically transparent and/or reflective objects, and hence the recording of volume images of the biological tissue in the observed field of view. Optical coherence tomography (OCT) essentially is an interferometric method using broadband light with a short coherence length. Systems for acquiring OCT data therefore comprise an interferometer and a broadband light source with a spectral width of more than 1% of the central wavelength.

OCT data can be acquired sequentially or in parallel. By way of example, sequential acquisition of OCT data is implemented by virtue of a low-coherent source light beam being split at a beam splitter into a sample beam and a reference beam which are sent through two arms of an interferometer, with a movable reference mirror being arranged in the reference beam path and the object to be examined being arranged in the object beam path. A path difference between object beam and reference beam, and hence the measured depth, can be set by displacing the reference mirror. The object beam is scanned over the sample in two dimensions by means of a mirror in the object beam path, allowing three-dimensional scanning of the sample as a result.

In the context of such an acquisition of OCT data in the time domain (time domain OCT-TD OCT), the spectral width of the light source $\Delta\lambda$ corresponds to a coherence length $L_c$ of $L_c=\lambda^*/\Delta\lambda$. The axial resolution of an OCT system corresponds to the coherence length $L_c$ of the utilized light and denotes the capability of resolving objects which have a spacing of at least the coherence length along the optical axis. By way of example, a light source in the near infrared range with a central wavelength of 800 nm and a spectral width of 80 nm has a coherence length of 7 µm and an OCT system having such a source consequently has an axial resolution of approximately 1-10 µm. The transverse resolution of an OCT system is determined by the optical unit used in the object beam path, in particular by the object lens focusing the light on the object to be examined.

A sequential acquisition of OCT data is also possible in the frequency domain (frequency domain OCT-FD OCT), with a distinction generally being made between the use of a tuneable source (swept source OCT) and the use of a dispersive detector (spectral domain OCT-SD OCT). The frequency of the excitation light source, frequently a laser, is tuned within the scope of swept source OCT, whereby it is possible to vary a path difference between sample beam and reference beam, and hence the scanned sample depth, even without a displaceable reference mirror. A broadband light source is likewise used in the case of SD OCT, but the detection is preceded by a separation of the frequency components of the interference signal, for example by an optical grating.

Slice and volume data of biological tissue are acquirable by means of OCT, and this can significantly increase the information content for a surgeon. Consequently, an integration of OCT in surgical microscopes is desirable in order to be able to display both video data of the surface of a desired field of view and depth and/or slice images of the field of view. To the extent that surgical systems have to date been able to supply volumetric OCT images, their recording times have been relatively long and, moreover, rendering has been restricted to postprocessing only for reasons of time and resources. Volume imaging in real-time during the operation was therefore not possible to date.

However, as OCT technology and the capability and speed of graphics processors (GPUs) have advanced, faster OCT methods for intraoperative imaging have become available. The representation of OCT volume images in real-time rendered possible thereby however opens up many different options for representing the acquired OCT signals, with methods to this end not yet being available. In particular, there is a lack of methods which allow a form of representation of the OCT signals optimized to medical or surgical applications. The use of suboptimal methods harbours the risk of overwhelming or distracting the user, which may have grave consequences especially in the case of surgeons.

The object of the present invention is to overcome or at least reduce the disadvantages of the prior art and to provide an improved system and an improved method for acquiring and visualizing OCT signals.

DESCRIPTION OF THE INVENTION

The object according to the invention is achieved by the subjects of the independent patent claims. Preferred developments are the subject matter of the dependent claims.

A first aspect of the present disclosure relates to a system for acquiring and for visualizing OCT signals, in particular for acquiring and visualizing such signals by means of a medical device, for example a surgical microscope.

The system according to the present disclosure comprises an OCT system. The OCT system preferably comprises a broadband light source designed to illuminate a sample. This light source preferably is a tuneable (swept source) laser, for example a broadband laser, a super continuum laser and/or an ultrashort pulse laser. In this case, a tuneable laser at any given time can be a narrow bandwidth light source, the central frequency of which however is able to be varied over time in a targeted manner, or formed from a plurality of narrow bandwidth light sources. However, any other broadband source can also be used, for example a superluminescent diode, for example in FD-OCT.

Further, the OCT system preferably comprises an interferometer, for example a Michelson, Mach-Zehner or Koster interferometer, designed for creating and superposing a sample beam and a reference beam. The interferometer preferably comprises a beam splitter for creating and superposing the sample beam and reference beam from the light of the broadband source, a reference beam path and a sample beam path. Further preferably, the interferometer comprises means for adjusting an examined sample depth. Depending on the measurement method, this may be a means for creating a path difference (for instance, a displaceable mirror in the reference beam within the scope of SD-OCT), a means for separating light of a certain path difference (for instance, an optical grating within the scope of FD-OCT) or means for creating light of a certain path difference (for instance, a tuneable source in the case of a swept source OCT).

The OCT system also comprises a scanning mechanism designed to scan the sample with the sample beam. In particular, the scanning mechanism is designed to scan the sample beam over the sample in two dimensions. The scanning mechanism preferably is a scanning mirror but other scanning mechanisms may also be used, for example an optical fibre scanner, a prism scanner, a Palmer scanner or the like. A scanning mechanism is dispensable in the case of an OCT system configured for a full-field OCT.

The OCT system further comprises a detector designed to detect an interference pattern produced by the superposition of sample beam and reference beam. By way of example, the detector is a line detector, a two-dimensional detector array, a photodetector or a dispersive detector. By way of example, the detector is in the form of a CCD or CMOS detector.

The system according to the present disclosure further comprises a display means designed for the time-resolved display of image data. The display means preferably is one or more visual display units, for example at least one visual display unit of a surgical microscope, a visual display unit fixedly installed within an operating theatre or a head-mounted display (HMD), for example a pair of video glasses. The visual display unit preferably is a 4K- and/or 8K-capable visual display unit and/or a 3-D visual display unit designed for a stereoscopic representation.

The system according to the present disclosure also comprises a control unit which is connected to the OCT system and the display means, in particular for one-directional or bidirectional data transfer. The control unit is configured to drive the OCT system to acquire a time-resolved OCT signal from a selected field of view (region of interest—ROI) of a sample. By way of example, the sample is an operating site on a patient, especially an eye in the case of ophthalmological operations. However, the sample may also be any other operating site, for example brain tissue in neurosurgery, tissue located in the ENT region in the case of ENT surgery or the gingiva, tartar or dental nerves in the case of dental surgery. This may likewise relate to any other tissue or preparation (in vivo, in vitro or in situ). The field of view is preferably selected by a user. The time-resolved OCT signal is preferably acquired by virtue of a light signal being created and steered in part to the sample as a sample beam by means of the interferometer and being superimposed in the interferometer on a reference beam, likewise created from the light signal, in order to create an interference pattern.

The control unit of the system according to the present disclosure is further designed to determine a time-resolved OCT image on the basis of the acquired time-resolved OCT signal and a specifiable virtual viewing direction. The OCT signal is an interference signal, with the modulation of the envelope of the interference signal encoding reflection properties of the sample. The scanning mechanism allows the sample to be scanned in two dimensions at a sample depth set by way of the path difference. A clock frequency (image refresh rate) for the time-resolved OCT signal arises from the utilized scanning mechanism, the utilized means for selecting or creating the path difference, for example an adjustable mirror in the reference beam, an optical grating upstream of the detector or a tuneable broadband light source, and the refresh rate of the detector. The control unit determines a time-resolved OCT image on the basis of the OCT signal by calculation, for example by means of volume rendering, ray tracing and/or ray marching. To this end, the control unit initially determines a virtual viewing direction and takes account of this virtual viewing direction when determining the OCT image by means of volume rendering, ray tracing and/or ray marching. Consequently, an OCT image is determined by the system according to the present disclosure on the basis of the OCT signal and a specifiable virtual viewing direction, whereby a degree of freedom for the perspective determination of the OCT image, provided by the OCT system, is advantageously usable. In this case, the virtual viewing direction differs from an actual viewing direction of a user as a matter of principle. Instead, the virtual viewing direction represents a spatial direction which is specifiable by the user as described hereinbelow and/or determinable as indicated hereinbelow on the basis of device parameters and which serves as a basis for the calculation of the OCT image.

The control unit of the system according to the present disclosure is also configured to display the determined time-resolved OCT image on the display means. In this case, the display is advantageously in the virtual viewing direction. Here, the virtual viewing direction is preferably set for a defined period of time. The virtual viewing direction can likewise preferably be set in the form of a sequence and for example changes automatically once a predefined time has expired, when a predefined user input (for example, an actuation of a foot pedal) is detected, when a state or positional change of a medical instrument is determined, when a change in a device parameter is determined and/or when a change of a phase of a performed operation is recognized. The virtual viewing direction likewise preferably follows a user input continuously or discontinuously, for example on the basis of a detected actual viewing direction of the user. Thus, for example, an inclination of the head of the user can be detected and the OCT image can be created with a corresponding inclination and displayed on the display means. The system according to the present disclosure therefore advantageously enables an optimal visualization of the OCT signal in accordance with the needs of the user, whereby the potentials of the OCT signal are optimally exploited and a maximum information content is made available to the user.

In a preferred embodiment of the system according to the present disclosure, the virtual viewing direction is defined by an azimuth angle and an elevation angle relative to the optical axis of the OCT system. Here, the optical axis of the OCT system preferably corresponds to an optical axis of a surgical-microscopic system (explained hereinbelow) of the system according to the present disclosure and/or is preferably perpendicular to a surface of the sample. The azimuth angle preferably describes an angle between 0° and 360° in a plane perpendicular to the optical axis, preferably in the plane of the sample surface. The azimuth angle is a plane angle and is measured between a zero and a projection of the virtual viewing direction into this plane. Therefore, the azimuth angle defines a virtual viewing direction in the narrower sense. The elevation angle preferably describes an angle between 0° and 90° in a plane containing the optical axis, preferably in a plane orthogonal to the sample surface. The elevation angle is a plane angle and for example measured between the virtual viewing direction and the sample surface. The elevation angle therefore defines a vertical viewing angle.

In a further preferred embodiment of the system according to the present disclosure, the control unit is configured to determine the time-resolved OCT image as a three-dimensional volume image from the perspective of the virtual viewing direction. In addition to the representation of OCT images in an "en-face" representation, which is to say in a plan view, the control unit therefore also enables the perspective display of the OCT signals. Likewise preferably, the control unit is further designed to represent the OCT signals in the form of slice images in a height direction of the sample (so-called B scans). The display of the time-resolved OCT images as a perspective three-dimensional volume image from different perspectives advantageously allows the maximum of depth information about the object to be obtained. In particular, both the straight representation from the bird's eye view (plan view, "en face"), the latter from different virtual viewing directions (azimuth angle and elevation angle), and also sectional images (B scans) along different cut lines may be advantageous, for example in order to obtain the respectively relevant information about the sample during different phases of an intervention.

In other words, the most advantageous virtual viewing direction may vary depending on application and situation during the operation, especially in the case of medical (e.g., ophthalmological) uses. Thus, it may be advantageous to initially display the time-resolved OCT images (4D-iOCT) from the technical viewing direction of a video from a surgical microscope (with the technical viewing direction being determined on the basis of a device parameter, for example), in order to offer the user the best overview. However, over the course of the further use or operation, other virtual viewing directions, for example lateral virtual viewing directions, may ensure far better depth information. The perspective arising as a result moreover corresponds to the natural perspective of the human view with the naked eye and therefore also offers an advantage for the microsurgical work.

The system according to the present disclosure preferably comprises an interface for acquiring a user input. The interface is preferably a hand switch or a foot switch. Likewise preferably, the interface is a means for recognizing a head movement and/or eye movement or an actual viewing direction, for example integrated into video glasses or into a head-mounted display, HMD. The interface may further be designed to capture voice commands and may comprise at least one microphone to this end. Likewise preferably, the interface is a keyboard, a joystick, a mouse, a touchscreen or a combination thereof.

According to this preferred embodiment, the control unit is further designed to control the interface for acquiring a user input. Further preferably, the user input is preceded by a prompt, output to the user by means of the output means for example. Likewise preferably, the user input is a selection of a plurality of predefined input options, which for example specify a virtual viewing direction, an operation to be carried out and/or an intervention to be carried out. Likewise preferably, the user input is a user input which is freely definable by the user within a given scope. Likewise preferably, the control unit is designed to assist the user with the user input, for example by displaying a plurality of dialogues for the targeted query of specific user inputs.

According to this embodiment, the control unit is further designed to determine the virtual viewing direction on the basis of the user input. Consequently, the user is advantageously able, in a targeted fashion, to select the virtual viewing direction considered to be optimal. Particularly preferably, the interface is used to acquire a user input which specifies the azimuth angle and the elevation angle, for example following a corresponding prompt for the user. Likewise preferably, azimuth and elevation angles are derived from the user input, for example from a viewing direction specified directly by the user by means of a head and/or eye control.

As an alternative or in addition, the system further comprises a device interface designed to acquire a device parameter. The device interface is preferably an interface for connecting a surgical-microscopic system, as still described in detail hereinbelow. Likewise preferably, the device interface however is also an interface for connecting any other imaging system. Further, the device interface can be an interface for connecting a medical instrument. Likewise preferably, a system for tracking a medical or medical engineering instrument is connectable via the device interface, wherein the tracking system may also be the surgical-microscopic system or any other imaging system. By way of example, the medical instrument is a pointer, a probe, a pair of tweezers, an awl, a phaco tip, an endoscope, an endo LED of a gripper or the like. According to this embodiment, the control device is preferably configured to communicate, in particular communicate bidirectionally, with the device interface and further configured to drive the device interface to acquire a device parameter of a device connected by means of the interface.

According to this embodiment, the control unit is further designed to determine the virtual viewing direction on the basis of a device parameter acquired by means of the device interface. Preferably, the device parameters of a connected surgical-microscopic system or other imaging system can be used to determine a technical viewing direction of the surgical-microscopic system or other imaging system and the virtual viewing direction can be set to be the same as the technical viewing direction. This enables multimodal image acquisition and display, with a virtual viewing direction of the OCT image advantageously corresponding to a (technical) viewing direction of the other image data.

Likewise preferably, the device parameter describes a pose, a position and/or a state of a medical (or medical engineering) instrument which is connected or tracked by means of the tracking system and the virtual viewing direction is determined on the basis of the pose, the position and/or the state of the medical (medical engineering) instrument. Thus, the virtual viewing direction can be determined, for example, corresponding to the pose of a pointer (optionally along the longitudinal axis of the pointer) or corresponding to the state of a gripper. In this case, the spatial pose of the medical instrument can be determined by the instrument itself and/or the spatial pose of the medical or medical engineering instrument can be determined by way of a tracking system. In this case, a medical instrument need not comprise any dedicated electronics; instead, the properties thereof can be determined for example purely by the tracking system, optionally assisted by markers arranged on the medical instrument. Likewise preferably, the (image) recognition of the medical instrument is initiated by a user input, wherein the user input can be implemented on the instrument itself or in any other way.

A device parameter relating to the state of a connected medical instrument, received by the device interface, preferably also comprises the actuation of an input means of the medical device, with the result that the device parameter in this case also represents a user input at the same time. Likewise preferably, various device parameters are considered together, for instance a pose of the medical instrument (for example determined by the instrument itself and/or by a tracking system) and the actuation of an input means of the medical instrument. Thus, for example, a sequence of virtual viewing directions corresponding to a sequence of poses of the instrument is advantageously acquirable. A device parameter describing the medical engineering or medical instrument can be received via the device interface from the instrument itself or from a tracking system. Further preferably, the azimuth and elevation angles of the virtual viewing direction, as described hereinabove, are derived from a received device parameter.

In a preferred embodiment of the system according to the present disclosure, an OCT signal comprises a multiplicity of (first) tuples, which each comprise (or represent) a volume element of the sample and a scattering intensity. In this case, the volume element of the sample is preferably represented by three spatial coordinates (for example x, y and z) and can for example be interpreted as a sample voxel. The tuple may include further values in addition to the scattering intensity. According to this embodiment, the display means comprises a multiplicity of pixels and the control unit is configured to determine the time-resolved OCT images in such a way on the basis of the (first) tuples, on the basis of the resolution of the display means and on the basis of the virtual viewing direction that certain pixels correspond to certain volume elements, which is to say that certain pixels display certain volume elements of the sample. In other words, the control unit determines a mapping of pixels of the display means and volume elements of the sample. In this case, this mapping may depend on further settings, for example a scanning resolution of the utilized scanning mechanism, but is preferably constant over time for a given selection of settings such as virtual viewing direction, zoom level and stereo angle. Therefore, the control unit realizes spatial registration between pixels of the display means and the OCT signals or the determined OCT images.

Further preferably, the control unit is configured to locally register, on the basis of acquisition parameters of the OCT system, the OCT signals acquired by the OCT system. In this context, a local registration of these signals denotes correct linking of these signals to a reference coordinate system, for example the coordinate system of the patient during an intervention, and enables a unique mapping of coordinates of the patient space on corresponding coordinates of the signal space. A registration of the signals preferably requires a calibration of the OCT system. The acquisition parameters of the OCT system preferably comprise calibration parameters. The acquisition parameters of the OCT system preferably take account of the scanning mechanism and/or the detector of the OCT system. On the basis of the local registration on the basis of the acquisition parameters, it is advantageously possible to correctly depict structures of the patient situated at defined coordinates of the patient space at the corresponding coordinates in the image space of the OCT images, especially with correct relative poses with respect to one another.

In a particularly preferred embodiment of the system according to the present disclosure, the said system further comprises a surgical-microscopic system designed to acquire a time-resolved image signal from the selected field of view of the sample. The surgical-microscopic system preferably comprises an optical unit, in particular for detecting light, for example visible light, reflected or back-scattered from the sample. By way of example, the optical unit comprises an objective lens and an eyepiece; however, it may moreover comprise further components, in particular further lens elements, mirrors, beam splitters and/or the like. The surgical microscopic system further comprises an image sensor which is designed to acquire a time-resolved image signal of the selected field of view (region of interest— ROI) of a sample. The optical unit and the image sensor are preferably formed in integrated fashion, for example as parts of a camera of a surgical microscope. According to this embodiment, the control unit is further designed and configured to determine video image data corresponding to the acquired time-resolved image signal. In particular, the time-resolved image signal is a multiplicity of signals assigned to surface elements of the sample, which are acquired sequentially or simultaneously for a specific scan of the sample surface, wherein the scan is determined by a scanning mechanism and/or the image sensor. Further, the time-resolved image signal has a clock frequency (image refresh rate), which is determined by a scanning mechanism and/or the image sensor. From this image signal, the control unit creates video image data with a raster (resolution) and an image refresh rate suitable for the display on the display means. The control unit is further configured to display the video image data by means of the display means.

In the system according to the present disclosure, an image signal preferably comprises a multiplicity of (second) tuples. In this case, each (second) tuple comprises (or represents) a surface element of the sample and at least one greyscale value. In this case, the surface element of the sample is preferably represented by two lateral spatial coordinates (for example x and y) and can for example be interpreted as a sample pixel. In addition to the greyscale value, which ultimately arises from a detected intensity, each (second) tuple may moreover also comprise colour values, for example within the scope of the detection of intensities for different colours by means of colour filters disposed upstream of the image sensor. According to this embodiment, the control unit is moreover configured to determine the video image data in such a way on the basis of the (second) tuples and on the basis of a resolution of the display means that certain pixels display certain surface elements of the sample. In other words, the control unit determines a (second) mapping of pixels of the display means and surface elements of the sample, in addition to the (first) mapping of pixels of the display means and volume elements of the sample. In this case, this (second) mapping may depend on further settings, for example a zoom level of the surgical-microscopic system, but is preferably constant over time for given settings. The (second) mapping preferably corresponds to the (first) mapping. Therefore, the control unit also realizes spatial registration between pixels of the display means and image signals (video image data) of the surgical-microscopic system.

Further preferably, the control unit is further configured to locally register, on the basis of acquisition parameters of the surgical-microscopic system, the image signals acquired by the surgical-microscopic system. A registration of the signals preferably requires a calibration of the surgical-microscopic system. The acquisition parameters of the surgical-microscopic system consequently preferably comprise calibration parameters and/or optical settings of the surgical-microscopic system, for example a focal length and/or a zoom level of an optical unit (camera) utilized. Moreover, the acquisition parameters preferably also comprise a set of intrinsic parameters of the surgical-microscopic system. In this case, the intrinsic parameters determine a relationship between the coordinate system of an image signal and the coordinate system of the associated imaging sensor. In this case, the type of the intrinsic parameters depends, in particular, on the type of imaging sensor utilized, with imaging sensor in this case denoting both the actual sensor and the utilized optics. In the case of a Tsai's camera calibration, the intrinsic parameters for example comprise an effective focal length, the coordinates of a principal image point (centre of the distortion) of an image signal, a first scaling factor and/or a first radial lens error coefficient (distortion coefficient). As an alternative to the aforementioned intrinsic parameters of Tsai's camera calibration, other intrinsic parameters can also be used, for example for Zhang's camera calibration (cf., for example, "*A practical comparison between Zhang's and Tsai's calibration approaches*", Li et al., Proceedings of the 29th International Conference on Image and Vision Computing New Zealand, November 2014 Pages 166-171, DOI: 10.1145/2683405.2683443).

The local registration of the OCT signals together with the local registration of the image signals advantageously enables the creation and display of the OCT images and the video image data, with the result that the created time-resolved OCT image corresponds at least to one portion of the displayed video image data. Preferably, an OCT signal is acquired from the entire field of view and an OCT image is created from at least a part of the field of view. Likewise preferably, an OCT signal is acquired from a portion of the field of view and an OCT image is created from at least a part of the portion of the field of view. The control unit is further configured to display the time-resolved OCT image on the display means at the position of the portion of the video image data. Preferably, video image data and an OCT image are created from the entire field of view and are each displayed on the entire display means. Likewise preferably, an OCT image is created from a portion of the field of view and displayed on the display means at the position of the video data corresponding to this portion of the field of view. In other words, video image data and OCT images corresponding to the same portion of the sample are displayed at the same location on the display means. The system according to the present disclosure consequently enables a seamless integration of video image data and OCT images on the display means, whereby an easier observation of the multimodal image data is enabled for a user. This allows the multimodal image data to be observed without moving the head or the eyes, which has an advantageous effect on the attentiveness of the surgeon, in particular in the case of imaging during operative interventions.

The control unit of the system is preferably configured to simultaneously display the video image data and the time-resolved OCT image on the display means. This particularly advantageously allows the simultaneous consideration of both image modalities by a user. To nevertheless allow a distinction to be made between the different image data, the control unit is further preferably configured to display the video image data with a first level of transparency and the time-resolved OCT image with a second level of transparency. In this case, the first and the second level of transparency preferably differ from one another. The first and the second level of transparency likewise preferably vary over time. By way of example, the image signal is initially displayed with a transparency of 0% while the OCT image is displayed with a transparency of 100%. Over the course of time, the transparency of the image signal is then adjusted continuously from 0% to 100% while the transparency of the OCT image is simultaneously adjusted from 100% to 0%. Consequently, this ensures a continuous transition between the display of the video image and of the OCT image.

In a likewise preferred embodiment of the system according to the present disclosure, the control unit is also designed to locally register the video image data and OCT images by means of an image analysis. In this case, a local registration of these image data denotes correct linking of these images in a common image coordinate system. The registration on the basis of the image data consequently allows relative linking of the image data for an image representation of the same structures that is as congruent as possible. By way of example, structure or tissue boundaries can be recognized in the video image data and the OCT images by means of image analysis, for example edge detection or the like, and can be compared to one another. These structures can then be overlaid on one another on the display means by way of a translational displacement, rotation and/or scaling. The local registration of the image data is preferably implemented in addition to a local registration of the acquired signals as described hereinabove.

In a likewise preferred embodiment of the system according to the present disclosure, the control unit is configured to display the video image data and the time-resolved OCT image sequentially on the display means. In other words, only one of the video image data and OCT images is depicted at any one time, at least at a specific location on the display means. This advantageously allows a clear distinction to be made between video image data and OCT data and likewise advantageously allows a simultaneous display of the various image data at different locations on the display means.

Particularly preferably, the control unit is configured to display the video image data and the time-resolved OCT image with the same magnification, the same perspective and/or the same stereo angle. In the case of a simultaneous display of both video image data at the same location of the display means, this preferably enables a perfect overlay of both image data and may advantageously enable a display with an optimized contrast. In the case of a sequential display, there preferably is a display with the same magnification, the same perspective and/or the same stereo angle at the transition between the locally registered image data. Consequently, there is a fluid transition between the displays of the image data. There can only be a display of the surface (plan view) in the case of the video image data. By way of example, this corresponds to an "en face" OCT image. As soon as there has been a transition from video image data to OCT image, the magnification, perspective and/or the stereo angle is further preferably adaptable in order to advantageously enable an improved view with an optimal depth perception. In particular, there can be a change from the initial "en face" view to a perspective display, for example by way of a continuous transition of the virtual viewing direction, or to a slice view (OCT B scan). Consequently, the perfect view is advantageously ensured in various phases.

According to a further preferred embodiment of the system according to the present disclosure, the display means is preferably designed to display image data stereoscopically. The display means preferably is a display means designed to display image data with different (e.g., orthogonal) polarizations, in combination with polarization glasses. Encoding the stereoscopic image data by colour filtering and combining 3-D glasses with colour filters is likewise preferred. However, the display means might also be a 3-D visual display unit, for example a light-field monitor or the like. According to this preferred embodiment, the control unit is further configured to determine a time-resolved first OCT image and a time-resolved second OCT image on the basis of the time-resolved OCT signal, the virtual viewing direction and a stereo angle, and to stereoscopically display the first OCT image and the second OCT image on the display means. In this case, the stereo angle is decisive for the depth impression within the scope of the image visualization on the display means. In the case of a stereo camera, the stereo angle corresponds to the angle between the optical axes of the individual cameras of the stereo camera, and therefore depends on the distance of the cameras from one another and on the working distance of the cameras from the object (sample).

Such a stereo angle forms a basis of the creation of the stereoscopic OCT images by calculation, enabling variable setting of the stereo angle. As a rule, a large stereo angle corresponds to strong depth perception (like when the human eye perceives close objects) and a small stereo angle generally corresponds to a low depth perception (like when the human eye perceives distant objects). Consequently, the system according to the present disclosure advantageously enables a display of the OCT images with a variable depth impression.

In a preferred embodiment of the system according to the present disclosure, the control unit is configured to determine the stereo angle on the basis of a user input acquired by means of the interface. Consequently, a user, for example a surgeon, can advantageously adjust a stereo angle on an individual basis, with the result that taking account of the user input when determining the stereo angle can advantageously also account for subjective preferences.

In a further preferred embodiment of the system according to the present disclosure, the control unit is further configured to determine the stereo angle on the basis of optical parameters of the surgical-microscopic system. In this case, the optical parameters of the surgical-microscopic system are acquired or read in the form of metadata by the control unit of the system according to the present disclosure. Consequently, the control unit is advantageously always informed about variable and fixed optical parameters of the surgical-microscopic system. In this case, the fixed optical parameters preferably characterize components of the surgical-microscopic system, for example utilized lens elements, eyepieces or the like, and the variable optical parameters in this case characterize preferably adjustable variables, for example a field of view, a resolution, an inclination of the optical axis and the like. Taking account of the optical parameters of the surgical-microscopic system advantageously allows a simultaneous display of OCT images and video image data with an optimal adaptation of the image data to one another and, likewise, a sequential display of OCT images and video image data with an optimal transition.

In a particularly preferred embodiment of the system according to the present disclosure, the surgical-microscopic system comprises a stereo camera with a first stereo lens (in combination with a first image sensor) which is arranged along a first optical axis and designed to acquire a first image signal of the field of view and with a second stereo lens (in combination with a second image sensor) which is arranged along a second optical axis and designed to acquire a second image signal of the field of view. The surgical-microscopic system is therefore designed to acquire stereoscopic time-resolved image signals. In this case, the first optical axis and the second optical axis of the surgical-microscopic system include an angle, with this angle between the optical axes, together with the working distance between the sample and the lenses, determining the stereo angle of the stereoscopic image acquisition in the surgical-microscopic system. According to this embodiment, the control unit is preferably designed to determine the stereo angle which forms the basis of the determination of the first OCT image and the second OCT image and which corresponds to the stereo angle of the surgical-microscopic system. Further, the control unit is preferably designed to determine first video image data on the basis of the first image signal and second video image data on the basis of the second image signal. Consequently, this embodiment advantageously enables a stereoscopic display of both the video image data and the OCT images with corresponding stereo angle. This advantageously allows a stereoscopic simultaneous display with minimal deviations and a stereoscopic sequential display with an optimal transition between the various image modes (video and OCT image data). According to this embodiment, the optical parameters of the surgical-microscopic system are or comprise at least the parameters of the surgical-microscopic system which influence a stereo angle of same.

In a likewise preferred embodiment, the control unit is designed to determine the stereo angle on the basis of a zoom level and/or a working distance of the stereo camera. In this case, the spacing between the cameras of the stereo camera is preferably fixed, with the result that the stereo angle only depends on the working distance of the cameras from the sample. This working distance is preferably determinable on the basis of the zoom level, for example in combination with the size of an imaged field of view or marker. If the spacing between the cameras of the stereo camera is designed to be variable, for example in the case of cameras positionable by way of a camera travel, then the spacing of the cameras is preferably also taken into account when determining the stereo angle. According to this embodiment, the control unit is preferably designed to determine the stereo angle of the surgical-microscopic system at least on the basis of the zoom level and/or working distance and to also use this stereo angle for the OCT images.

In a likewise preferred embodiment, the zoom level is also taken into account independently of the working distance. By way of example, the use of a small stereo angle is preferable when displaying a field of view using the surgical-microscopic system and a small zoom value. As a rule, a small zoom value corresponds to a large field of view, with a display of a strong depth impression generally not being desired. The use of a large stereo angle is preferable when displaying a field of view using the surgical-microscopic system and a large zoom value. A large zoom value corresponds to a small field of view, in which a detailed display with a strong depth impression is frequently desired. Consequently, a depth impression in the display of the determined OCT images is advantageously also increased in the case of large magnifications.

In a further preferred embodiment of the system according to the present disclosure, the control unit is configured to determine a phase of a performed operation and to determine the stereo angle on the basis of the phase of the performed operation. To this end, the control unit is preferably connected to a memory, in which a trained machine learning algorithm, for example a neural network (CNN) or the like, is stored. This algorithm was preferably trained by means of a multiplicity of video image data and/or OCT images or image signals and/or OCT signals, which were assigned a corresponding phase of an operation as a classification within the scope of the training. Accordingly, the trained algorithm is able to independently recognize a phase of an operation as a classification on the basis of video image data and/or OCT images or image signals and/or OCT signals. Preferably, the control unit according to this embodiment is designed to select a stereo angle corresponding to the determined phase of the operation. The stereo data suitable for different phases of the operation are preferably stored in a lookup table (LUT) in a memory or are likewise determined using a machine learning algorithm. By way of example, the latter can be trained by virtue of a multiplicity of video image data and/or OCT images or image signals and/or OCT signals being assigned a corresponding phase of an operation and/or a corresponding stereo angle as one or more classifications during the training.

In the case of a cataract operation, the operation phases may for example comprise: rest state, incision, injection of the ophthalmic viscosurgical device (OVD), capsulorhexis, hydrodissection, phacoemulsification, rinse/aspiration, implantation of the intraocular lens, close/moisturize the wound, non-operation. In the case of a refractive operation, the operation phases may for example comprise: idling, docking, applanation, application of the eye/CG rotation, lens cut, lens side cut, flap cut, flap side cut, uncover the eye, transition to the surgical microscope, positioning of the surgical microscope, open the incision, define the planes, sever the flap bed, sever the lens bed, remove and/or inspect the lenses, wipe, rinse, slit lamp, remove the speculum. In the case of a dental intervention, the surgical phases may for example comprise: access, extirpation, debridement, drying, obturation, restoration. It should be noted that all or only some of these phases may be part of the corresponding operation and that further operation phases may also be present and/or some phases may be omitted.

In a further preferred embodiment of the system according to the present disclosure, the latter further comprises a medical instrument. By way of example, the medical instrument is a probe, a pointer, a pair of tweezers, an awl, a phaco tip, an endoscope, an endo LED or the like.

According to this embodiment, the control unit is further configured to determine a position, a type and/or a state of the medical instrument. In this case, a type of the medical instrument can be implemented preferably on the basis of a device interface for connecting the medical instrument, by means of a tracking system (e.g., by identifying a target ID) and/or on the basis of an input via a user interface. Likewise preferably, a type of the medical instrument introduced into the field of view of the surgical-microscopic system is identified by image analysis of the video image data, for example by means of segmentation and object recognition.

The position of the medical instrument is preferably determined on the basis of the detection of a marker and/or a target comprising a plurality of markers, wherein the marker may be a label on or a structure of the medical instrument. The marker and/or the target is preferably detected by means of the surgical-microscopic system and optionally using additional light sources (e.g., infrared LEDs) and/or following a registration/calibration of the medical instrument (e.g., by positioning the one tip of the medical instrument at a defined location).

A state of the medical instrument introduced into the field of view of the surgical-microscopic system is likewise preferably determined on the basis of image analysis of the video image data. By way of example, whether tweezers are opened or closed can be identified on the basis of the image data. Moreover, a user input for changing a state can be read by the control unit; for example, a user input for activating a phaco tip signals a change in the state thereof. Further, a sensor attached to the medical instrument can detect the change in the state of the latter, for example tweezers being closed, and can transmit a corresponding sensor signal to the control unit.

According to this preferred embodiment, the control unit is further configured to determine a stereo angle for determining the stereoscopic OCT images on the basis of the position, the type and/or the state of the medical instrument. A change in the state of the medical instrument of a certain type and/or at a specific location is preferably indicative for a certain phase of an operation. Consequently, recognizing position, the type and/or the state of the medical instrument can be used to choose the optimal display type for this phase. In addition to the choice of the stereo angle, this optionally also comprises a change of further display parameters of the OCT image data, for example a zoom level, a virtual viewing direction, a displayed depth and/or a cut direction.

By way of example, using the aforementioned information, the control unit is able, either automatically or on the basis of a user input, to determine that a performed intervention is membrane peeling by means of tweezers and, in this case, to further determine a distance or a position of the tweezers relative to the eye and to adapt or set a virtual viewing direction and/or a stereo angle of the display of the OCT images on the basis of the aforementioned determinations. In a further example, the control unit is preferably able, either automatically or on the basis of a user input, to determine that a performed intervention is a subretinal injection of a "bleb" or a placement of a retinal stent and, on the basis thereof, to adapt a virtual viewing direction and/or a stereo angle so that a user is optimally assisted when positioning the needle or the stent, for example by virtue of a perspective illustration with a large depth impression (stereo angle) being chosen.

The functionalities of the control unit according to the invention can be implemented by electrical or electronic devices or components (hardware), by firmware (ASIC) and/or can be realized by carrying out a suitable program (software). Preferably, the functionalities of the control unit according to the invention are realized or implemented by a combination of hardware, firmware and/or software. By way of example, individual components of the control unit according to the invention for carrying out individual functionalities are in the form of a separately integrated circuit or are arranged on a common integrated circuit.

The individual functionalities of the control unit according to the invention are further preferably in the form of one or more processes which run on one or more processors in one or more electronic computers and which are generated when carrying out one or more computer programs. In this case, the control unit is designed to cooperate with the other components, in particular the user interface, the OCT system and the display means, in order to implement the functionalities of the system according to the invention as described hereinbelow. It is further evident to a person skilled in the art that the functionalities of a plurality of computers (data-processing devices, control units, controllers) can be combined or can be combined in a single device, or that the functionality of a certain data-processing device may be available distributed over a multiplicity of devices in order to realize the functionalities of the control unit according to the invention.

In a particularly preferred embodiment of the system according to the invention, the latter is integrated in a surgical microscope. In this case, the surgical microscope preferably comprises an OCT system as described hereinabove. Further preferably, the surgical microscope comprises, or is connected to, an interface for user input and a display means. Preferably, the surgical microscope further comprises a surgical-microscopic system as described hereinabove, wherein the image sensor and optical unit are part of a camera, in particular a main observer camera or a surround camera of the surgical microscope. The control unit of the surgical microscope is preferably designed as control unit of the system according to the invention and, in particular, designed to carry out the method according to the invention, as described hereinbelow, on the basis of commands stored on a storage unit of the surgical microscope.

Within the scope of the present disclosure, a surgical microscope is understood in the broadest sense to be a microscope suitable for use during an operation. The surgical microscope preferably has a mount which allows imaging of the operating region independently of head movements of the surgeon. Further preferably, the surgical microscope comprises at least one beam splitter and at least two eyepieces. Alternatively, the surgical microscope is a pure "digiscope" without eyepieces. Likewise preferably, the surgical microscope comprises at least one imaging sensor. Further preferably, the surgical microscope comprises a main observer camera and a surround camera. The surgical microscope may comprise kinematic or robotic aids for carrying out surgical interventions. As an alternative, a surgical microscope may be denoted a medical engineering microscope, a medically approved microscope or a medical microscope.

A further aspect of the present disclosure relates to a method for acquiring and visualizing OCT signals. The latter includes the method step of acquiring a time-resolved OCT signal of a selected field of view of a sample by means of an OCT system (as described hereinabove). In this case, the OCT signal comprises a multiplicity of tuples, which each comprise or represent a volume element of the sample and a scattering intensity corresponding to the volume element. The method further includes the steps of determining a given virtual viewing direction and determining, on the basis of the tuples, a resolution of a display means and the virtual viewing direction, a time-resolved OCT image as a three-dimensional volume image from the perspective of the virtual viewing direction. The method according to the present disclosure finally includes the display of the time-resolved OCT image on the display means, as a volume image from the perspective of the virtual viewing direction. The method according to the present disclosure realizes the same advantages as the system according to the present disclosure, and, in this respect, reference is made to the explanations given hereinabove.

In a preferred implementation of the method according to the present disclosure, the latter further includes the step of determining a time-resolved first OCT image and a time-resolved second OCT image. In this case, the first and the second OCT image are each determined on the basis of the tuples, on the basis of the resolution of the display means, on the basis of the viewing direction and additionally on the basis of a stereo angle, to be precise respectively as a three-dimensional volume image from the perspective of the virtual viewing direction. According to this implementation, there further is a stereoscopic display of the time-resolved first OCT image and time-resolved second OCT image on the display means. This advantageously allows the stereoscopic display with a variable virtual viewing direction and a variable stereo angle.

In a further preferred implementation of the method according to the present disclosure, the latter further comprises the step of determining a given virtual viewing direction on the basis of a user input acquired by means of an interface and/or on the basis of a device parameter acquired by means of a device interface.

Further preferred implementations of the method according to the present disclosure correspond to further preferred embodiments of the system according to the present disclosure and realize the same advantages as the embodiments.

A further aspect of the present disclosure relates to a computer program comprising commands which, when executed by a control unit as described hereinabove, preferably of a surgical microscope as described hereinabove, cause the system or surgical microscope as described hereinabove to carry out the method according to the invention as described hereinabove. The computer program preferably comprises commands which, when executed by a control unit as described hereinabove, preferably of a surgical microscope, cause the system or surgical microscope as described hereinabove to carry out the method according to the invention, in accordance with one of the preferred implementations, as described hereinabove. In this case, the computer program according to the invention is preferably stored in a volatile memory, for example a RAM element, or in a non-volatile storage medium, for example a CD-ROM, a flash memory or the like.

Further preferred embodiments of the invention will become clear from the other features set out in the dependent claims, and from the figures explained hereinbelow. The various embodiments of the invention that are set forth in this application can advantageously be combined with one another, unless specifically stated otherwise.

DESCRIPTION OF THE FIGURES

Figure 1:
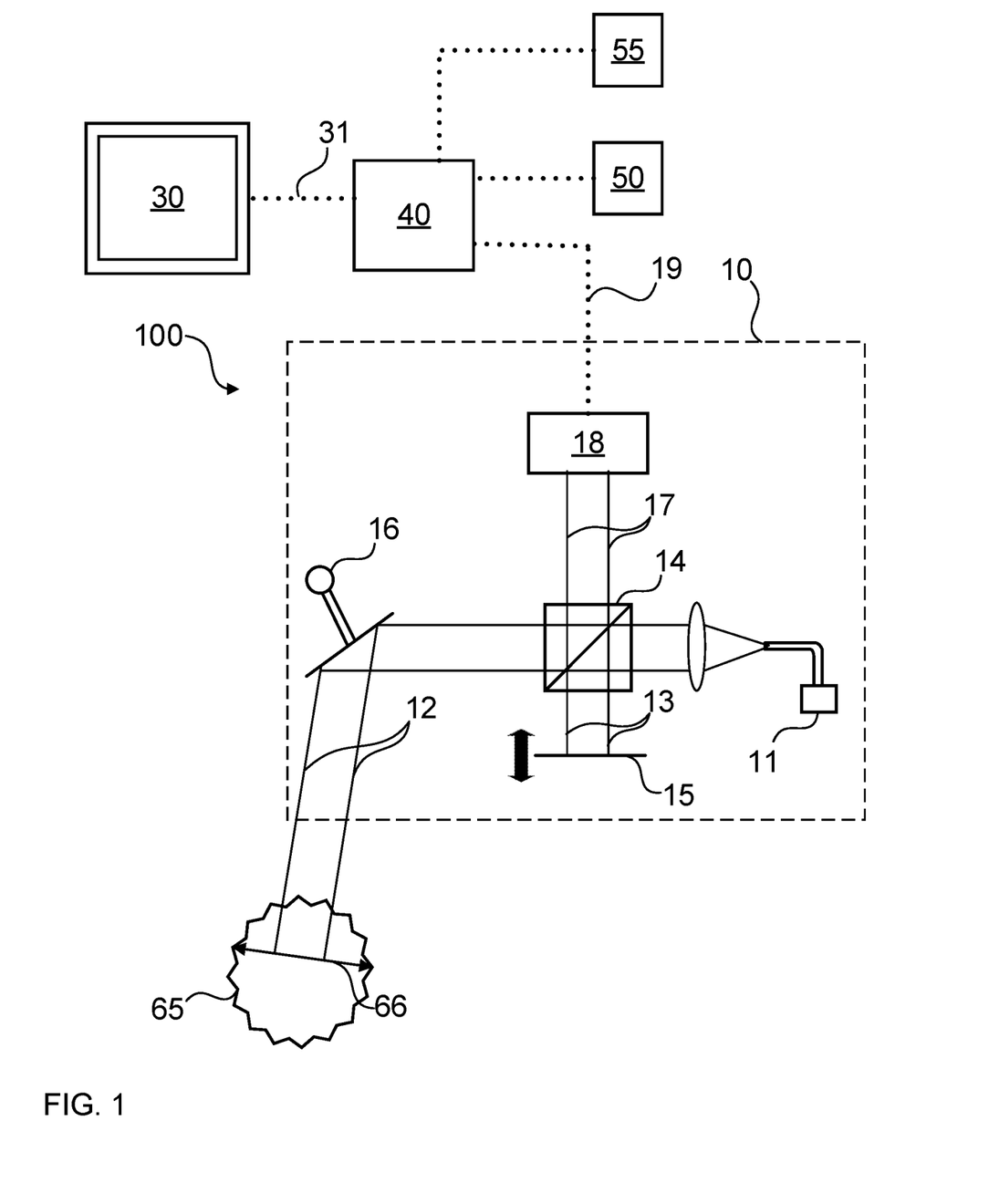
FIG. 1 shows a schematic illustration of a system according to a first embodiment.

The invention is explained below in illustrative embodiments and with reference to the attached drawings, in which:

FIG. 1 shows a schematic illustration of a system 100 for acquiring and visualizing OCT signals 19 according to a first embodiment.

The system 100 comprises an OCT system 10 having a broadband light source 11, for example a superluminescent diode. The light from the light source 11 is fed into an interferometer comprising a movable mirror 15 and a beam splitter 14. The light is split into a sample beam 12 and a reference beam 13 in the beam splitter 14. The sample beam 12 is scanned over the sample 65 by means of a scanning mirror 16, with at least one portion of a chosen field of view 66 of the sample 65 being scanned. The reference beam 13 is steered to the movable mirror 15 and reflected back to the beam splitter 14 thereby. The sample beam 12 interacts with the sample 65, in particular with the volume of the sample 65, and is scattered back thereby to the scanning mirror 16, which steers the said beam to the beam splitter 14. The back-scattered sample beam 12 and the reflected reference beam 13 are superposed there, with a path difference between the superposed beams 12, 13 being set by the movable mirror 15. The interference pattern 17 created thus is captured by means of a detector 18, for example a CCD detector or a CMOS detector.

The time-resolved OCT signal 19 acquired thus is transmitted from the detector 18 to the control unit 40. The control unit 40 further receives a user input regarding a desired virtual viewing direction by means of a user interface 50, this preferably being an HMD with a means for capturing a head movement and/or eye movement of a user. As an alternative or in addition, the control unit 40 receives a device parameter of a device connected by way of a device interface 55, for example of a surgical-microscopic system 20, of any other imaging system or of a medical instrument 70. Further, the device parameter may originate from a tracking system (not depicted here) connected to the device interface 55 but characterize a medical instrument, for example its spatial position.

For the acquired time-resolved OCT signal 19, the control unit 40 determines a time-resolved OCT image 31 on the basis of a given virtual viewing direction 60 and transmits the time-resolved OCT image 31 to the display means 30 for display purposes. In this case, the virtual viewing direction 60 is determined by the control unit 40 on the basis of a user input at the user interface 50 and/or on the basis of a device parameter determined by means of the device interface 55. Regarding explanations in relation to the virtual viewing direction 60, reference is made to the description hereinbelow of FIGS. 3 and 4.

Figure 2:
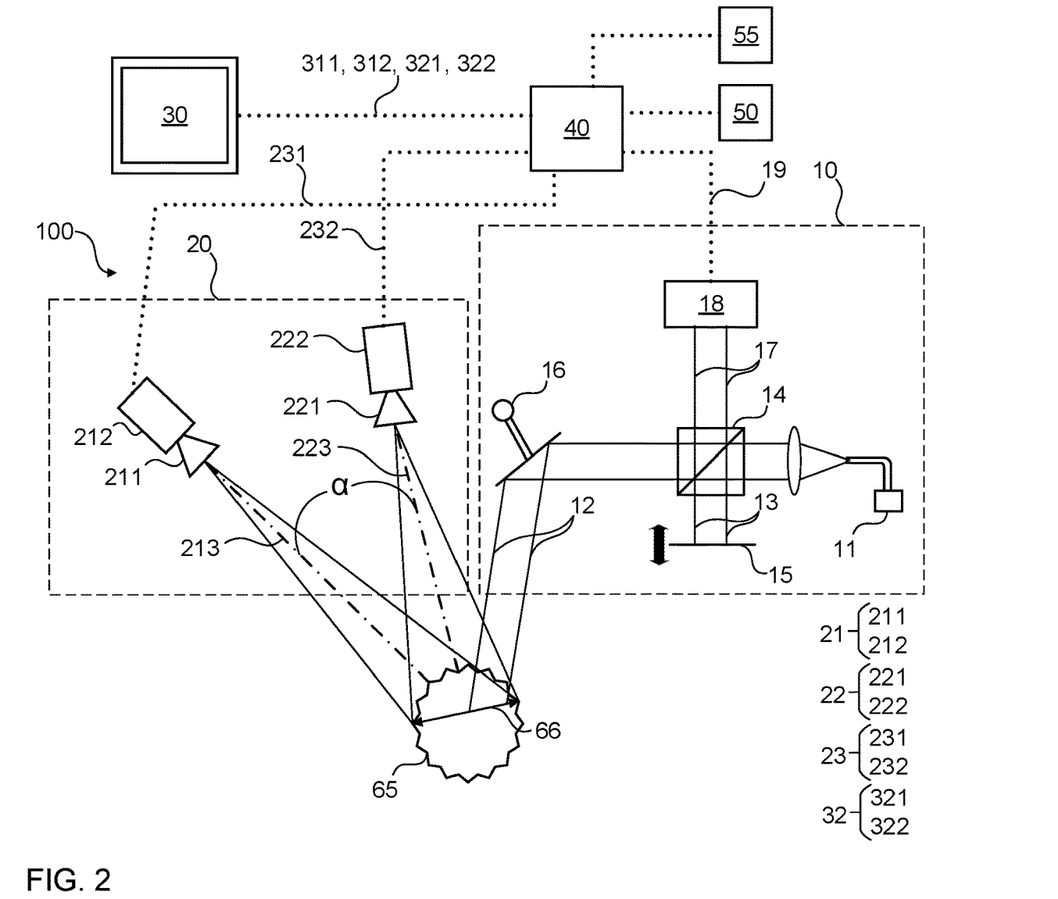
FIG. 2 shows a schematic illustration of a system according to a second embodiment.

FIG. 2 shows a schematic illustration of a system 100 for acquiring and visualizing OCT signals 19 according to a second embodiment. The same components are denoted by the same reference sign as in FIG. 1 and a repeated description of these components is dispensed with for reasons of conciseness.

The system 100 in FIG. 2 differs from that in FIG. 1 in that it further comprises a surgical-microscopic system 20 having a first camera 21 with a first optical unit 211 and a first image sensor 212 and having a second camera 22 with a second optical unit 221 and a second image sensor 222. Each of these cameras 21, 22 renders the field of view 66 of the sample 65 acquirable along an optical axis, and so a stereoscopic image signal 23 is captured as a result, the latter containing a first image signal 231 and second image signal 232. By way of example, the cameras 21, 22 are the two cameras of a main observer camera, designed as a stereo camera, of a surgical microscope.

According to the embodiment in FIG. 2, the control unit 40 determines stereoscopic video image data 32 corresponding to the acquired stereoscopic image signal 23, wherein a stereo angle $\alpha$ between the optical axes 213, 223 of the two cameras 21, 22 determines a depth impression or a depth perception of the stereoscopic video image data 32 created on the basis of the stereoscopic image signal 23. In this case, the stereoscopic video image data 32 comprise first video image data 321 corresponding to the first image signal 231 and second video image data 322 corresponding to the second image signal 232. In addition to the spacing of the cameras 21, 22, the stereo angle $\alpha$ depends on a working distance between the cameras 21, 22 and the sample 65.

In the system 100 of FIG. 2, a time-resolved OCT signal 17 is acquired in the same manner as has already been described with reference to FIG. 1. However, the control unit 40 uses the OCT signal 17 to determine a first OCT image 311 corresponding to the first video image data 321 and a second OCT image 312 corresponding to the second video image data 321. In this case, the first OCT image 311 and the second OCT image 312 are for example created as if these were captured at the same stereo angle $\alpha$ as the first and the second image signal 231, 232. However, a stereo angle of the OCT images 311, 312 can likewise also be set differently on the basis of a user input acquired by means of the interface 50. The first and second video image data 321, 322 are displayed simultaneously or sequentially on the display means 30 together with the first and second OCT images 311, 312, with a change between the OCT images 311, 312 and the video image data 321, 322 being implemented on the basis of an input by means of the interface 50, for example.

Figure 3:
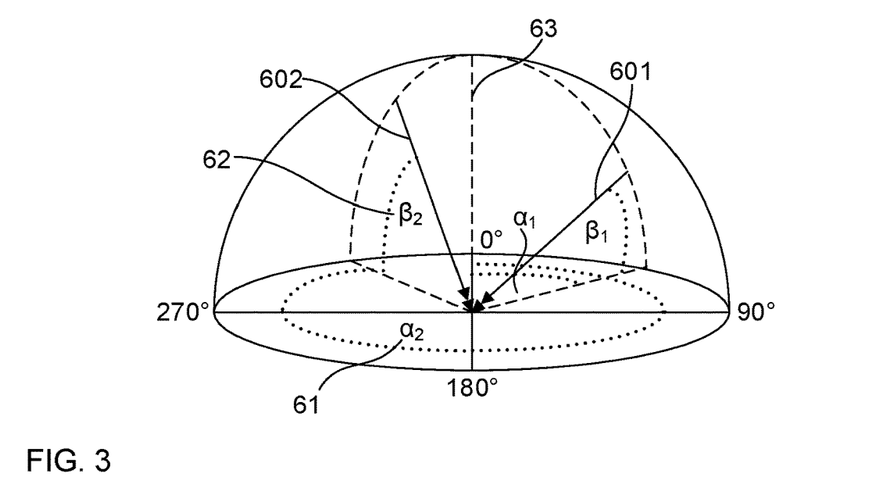
FIG. 3 shows a schematic illustration of a virtual viewing direction.

FIG. 3 shows a schematic illustration of a virtual viewing direction 60, in particular of a first virtual viewing direction 601 and a second virtual viewing direction 602. In this case, each of these virtual viewing directions 601, 602 is defined by an azimuth angle 61 and by an elevation angle 62 relative to an optical axis 63 of the OCT system 10. In this case, the optical axis of the OCT system 10 is preferably perpendicular to a surface of the sample 65. The azimuth angle 61 is a plane angle between 0° and 360° in a plane perpendicular to the optical axis 63. The elevation angle 62 is a plane angle between 0° and 90° in a plane containing the optical axis 63. The elevation angle is a plane angle and measured between the virtual viewing direction 601, 602 and the horizontal (sample) plane. In the illustration of FIG. 3, a first virtual viewing direction 601 is defined by a first azimuth angle $\alpha_1$ of approximately 45° and by a first elevation angle $\beta_1$ of approximately 30°, and a second virtual viewing direction 602 is defined by a second azimuth angle $\alpha_2$ of approximately 315° and by a second elevation angle $\beta_2$ of approximately 60°.

Figure 4:
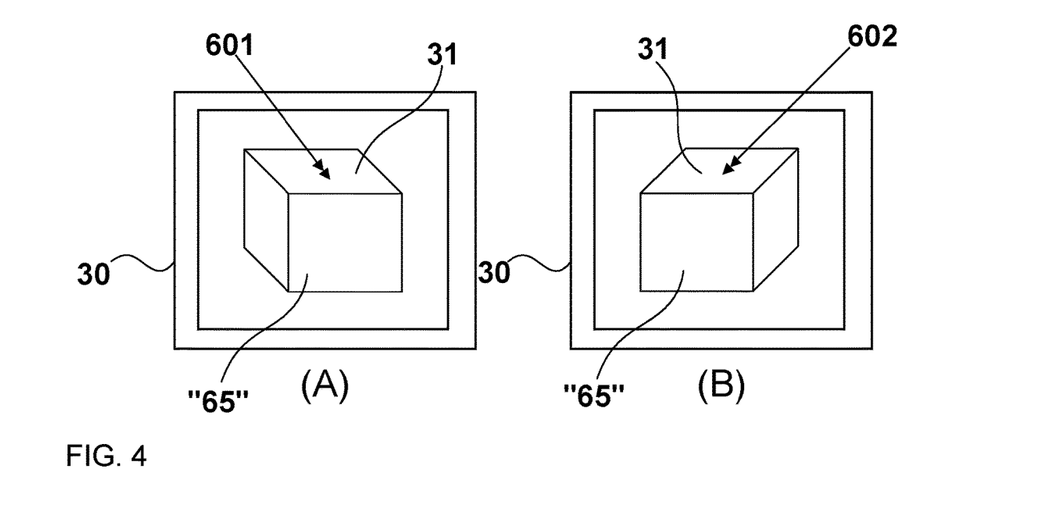
FIG. 4 shows a schematic illustration of a visualization of OCT signals as OCT images on the basis of a virtual viewing direction.

FIG. 4 shows a schematic illustration of a visualization of OCT signals 19 as OCT images 31 on the basis of a virtual viewing direction 60. In this case, FIG. 4(A) shows an OCT image 31 of the sample 65 (image of the sample "65") from a first virtual viewing direction 61 with the first azimuth angle $\alpha_1$ and FIG. 4(B) in this case shows a deviating OCT image 31 of the sample 65 (image of the sample "65") from a second virtual viewing direction 602 with the second azimuth angle $\alpha_2$. A display of the effect of the different elevation angles $\beta_1$ and $\beta_2$ was dispensed with for reasons of clarity.

Figure 5:
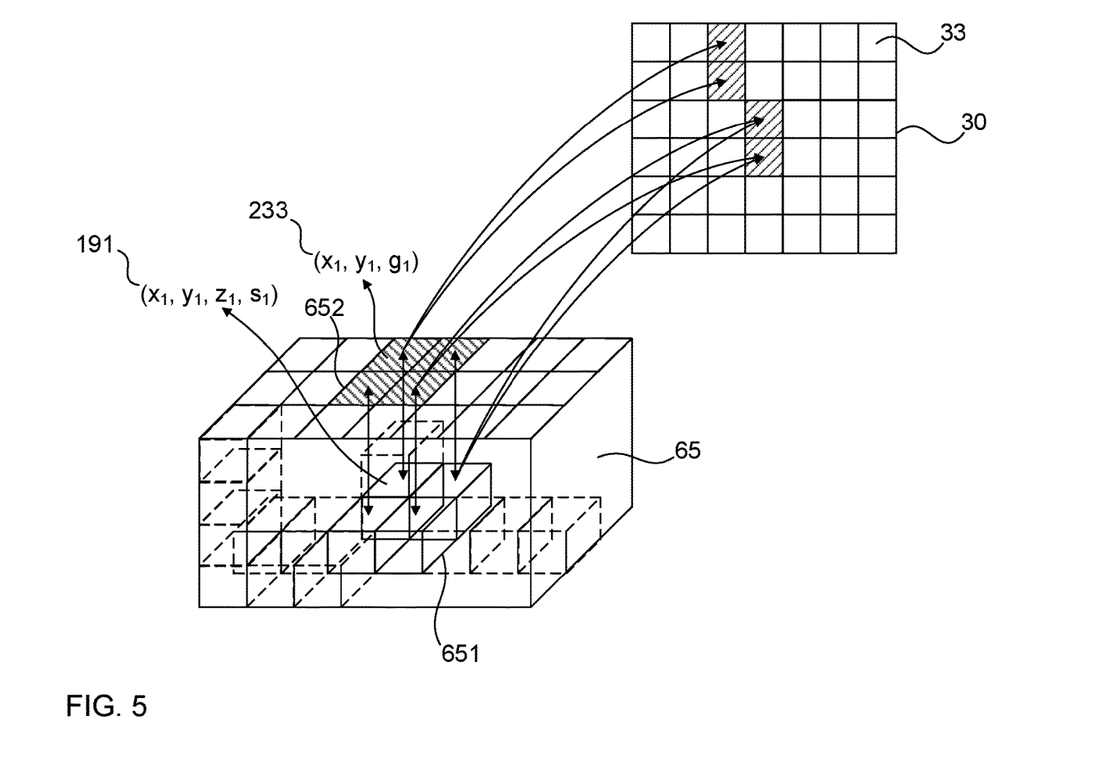
FIG. 5 shows a schematic illustration of a sample and a display means according to an embodiment.

FIG. 5 shows a schematic illustration of a sample 65 and a display means 30 according to an embodiment. In this case, the sample 65 comprises a multiplicity of volume elements 651 and a multiplicity of surface elements 652, with specific volume elements 651 corresponding to specific surface elements 652. An exemplary selection of surface elements 652 is depicted with hatching and while the plurality of the volume elements 651 are depicted using dashed lines, the four volume elements 152 corresponding to the hatched surface elements 652 are displayed using solid lines. Further, double-headed arrows connect these volume elements 651 to the associated surface elements 652.

The OCT system 10 of the system 100 of FIG. 1 in particular renders the volume of the sample 65 acquirable, by virtue of short wavelength light of the sample beam 12, scattered thereby, being superposed via the scanning mirror 16 on the reference beam 17 by means of the interferometer. The interference pattern 17 created thus, captured by means of the detector 18 as a time-resolved OCT signal 19, comprises a multiplicity of first tuples 191, with a number of the first tuples 191 for example arising from a number of the points on the sample 65 scanned by means of the scanning mirror 16. In this case, each of the first tuples 191 corresponds to one of the displayed volume elements 651 and comprises a value of a scattering intensity $s_i$. Further, each of the first tuples 191 is assigned three spatial coordinates $x_i$, $y_i$, $z_i$ on the basis of a calibration or registration of the OCT system 10 relative to a coordinate system of the sample 65 (patient). In the illustrated example, a first tuple 191 comprises the spatial coordinates $x_1$, $y_1$, $z_1$ and the scattered intensity value $s_1$.

The surface of the sample 65, in particular, is acquirable using the surgical-microscopic system 20 of the system 100 in FIG. 2 by virtue of long wavelength (visible) light reflected or scattered back from said surface being cast back to the image sensors 212, 222 of the cameras 21, 22 via the optical units 211, 221. The image signals 321, 322 acquired by means of the image sensors 212, 222 then each comprise a multiplicity of second tuples 233, with a number of the second tuples 233 in each case arising from a resolution of the associated image sensor 212, 222. Here, each of the second tuples 233 corresponds to one of the depicted surface elements 652 and comprises a greyscale value $g_i$ corresponding to an intensity of the light cast back to the respective image sensor 212, 222. Further, each of the second tuples 233 is assigned two lateral spatial coordinates $x_i$, $y_i$ on the basis of a calibration or registration of the image sensors 212, 222 relative to a coordinate system of the sample 65 (patient). In the illustrated example, a second tuple 233 comprises the lateral spatial coordinates $x_1$, $y_1$ and the greyscale value $g_1$.

The display means 30 also depicted in FIG. 5 comprises a multiplicity of pixels 33, in particular 42 pixels, with 7 pixels in the horizontal direction and 6 pixels in the vertical direction. In the illustrated example, the resolution of the image sensor 12 yielded an acquisition of the sample surface by the image signals 23 in 21 surface elements 652 with 7 surface elements 652 in the horizontal direction and 3 surface elements 652 in the vertical direction. Thus, in the video image data 32, one pixel 33 corresponds to one surface element 652 in the horizontal direction and two pixels 33 correspond to one surface element 652 in the vertical direction. Pixels 33 corresponding to surface elements 652 depicted with hatching are likewise depicted with hatching and the assignment is further elucidated by arrows. As likewise depicted by arrows, the control unit 40 of the system 100 also creates the associated OCT image 31 of the volume elements 651 corresponding to the surface elements 652 and depicts the said OCT image in the respective pixels 33 so that video image data 32 of certain surface elements 652 are depicted on specific pixels 33 and OCT images 31 of volume elements 651 corresponding to the surface elements 652 are likewise depicted on the specific pixels 33. Consequently, corresponding OCT images 31 and video image data 32 are depicted at the same location of the display means 30.

Figure 6:
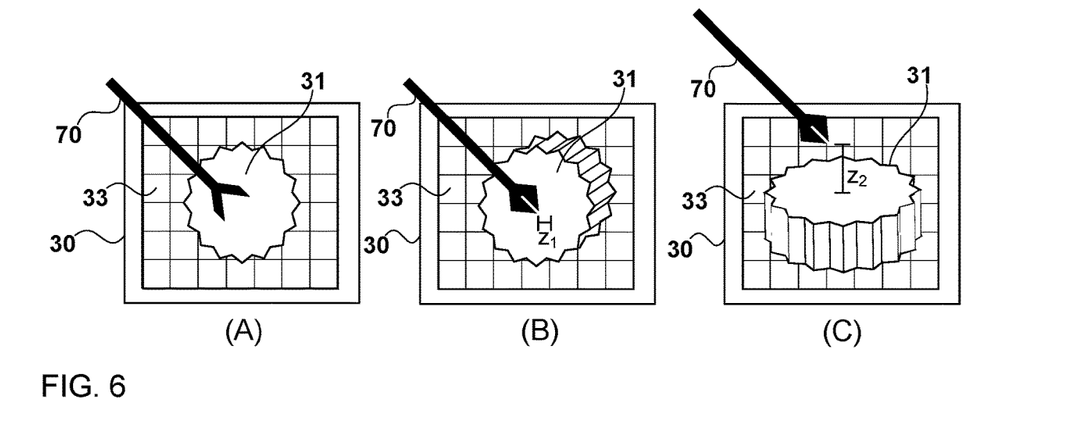
FIG. 6 shows a schematic illustration of a display means and a medical instrument according to a further embodiment.

A schematic illustration of a display means 30 according to a further embodiment is depicted in FIG. 6. In this case, the system 100 as depicted in FIG. 2 further comprises a medical instrument 70, in particular tweezers 70. In a phase where the tweezers 70 approach the sample 15, depicted in FIG. 6(A), the open tweezers 70 and the sample 15 are displayed on the display means 30 in the form of an OCT image 31 in an "en face" view (plan view), which is to say with an elevation angle of 90°, as depicted in FIG. 3. As soon as the control unit 40 recognizes, on the basis of sensor values and/or on the basis of an evaluation of the OCT images 31 or optionally video image data 32, that the tweezers 70 are closed and a vertical distance between the tip of the tweezers 70 and the surface of the sample 65 is less than or equal to a predetermined limit value $\Delta z_1$, the control unit 40 changes the display of the sample 65 and optionally of the tweezers 70 on the display means 30 from the "en face" view (plan view) to a different virtual viewing direction 60 by means of the OCT image 31. In particular, the control unit 40 determines an OCT image 31 as depicted in FIG. 6(B), specifically a perspective volume display with an elevation angle of approximately 45°. In the illustrated example, the tweezers 70 are used to lift or remove a part of the surface of the sample 65. As soon as the control unit 40 recognizes, on the basis of sensor values, the OCT image 31 and/or the video image data 32, that the tweezers 70 are closed and a vertical distance between the tip of the tweezers 70 and the surface of the sample 65 away from the lifted or removed surface of the sample 65 (e.g., laterally spaced apart by a minimum value) is greater than or equal to a predetermined limit value $\Delta z_2$, the control unit 40 changes the virtual viewing direction 60 of the display of the OCT image 32 again. As depicted in FIG. 6(C), this is now shown in a lateral perspective, which is to say with an elevation angle of close to 0°, on the display means 30. Consequently, an interaction of surgeon and surgical microscope is continuously and objectively improved by the advantageous display of the acquired OCT signal 19, by virtue of the virtual viewing direction 60 of the display being improved on the basis of a user input acquired by means of the interface 50.

Figure 7:
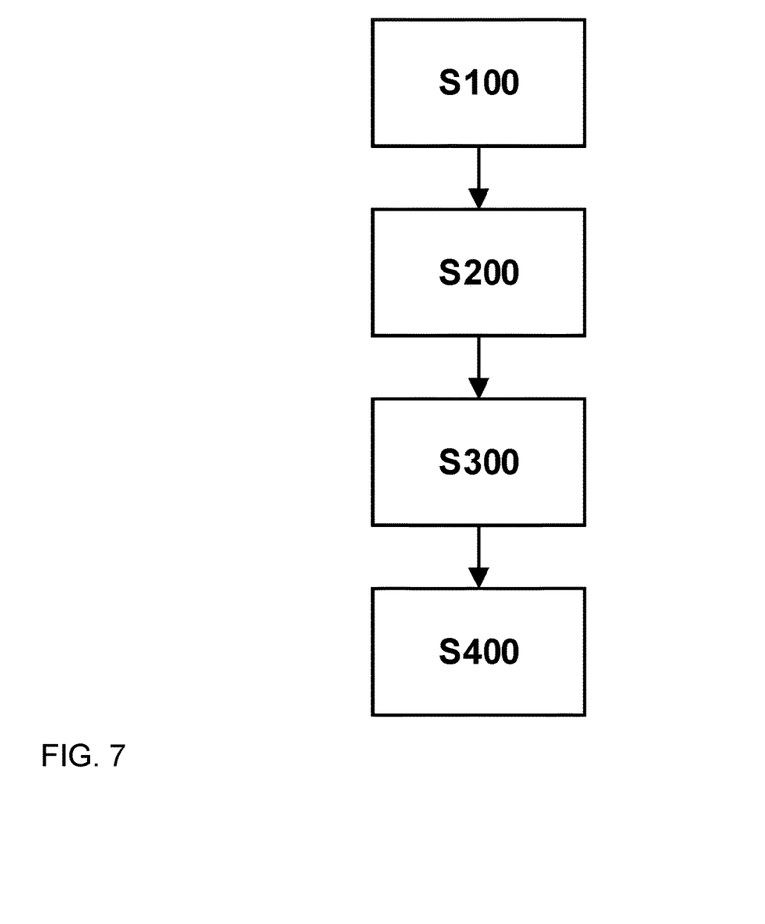
FIG. 7 shows a schematic flowchart of a method according to an implementation.

FIG. 7 shows a schematic flowchart of a method according to an implementation. The method includes a first step S100 of acquiring a time-resolved OCT signal 19 of a selected field of view 66 of a sample 65 by means of an OCT system 10, wherein the OCT signal 19 comprises a multiplicity of tuples 191 each representing a volume element 651 of the sample 65 and a scattering intensity corresponding to the volume element 651. The method further includes the second step S200 of determining a given virtual viewing direction 60. In a third step S300, a time-resolved OCT image 31 is determined on the basis of the tuples 191, a resolution of a display means 30 and the virtual viewing direction 60 as a three-dimensional volume image from the perspective of the virtual viewing direction 60. Finally, the time-resolved OCT image 31 is displayed on the display means 30 in a fourth step S400.

LIST OF REFERENCE SIGNS

10 OCT system
11 Broadband light source

12 Sample beam
13 Reference beam
14 Beam splitter (interferometer)
15 Movable mirror (interferometer)
16 Scanning mechanism (scanning mirror)
17 Interference pattern
18 Detector
19 Time-resolved OCT signal
191 Tuple (OCT)
20 Surgical-microscopic system
21 First camera
211 First optical unit
212 First image sensor
213 First optical axis
22 Second camera
221 Second optical unit
222 Second image sensor
223 Second optical axis
23 Time-resolved image signal
231 First image signal
232 Second image signal
233 Tuple (image signal)
30 Display means
31 OCT image
311 First OCT image
312 Second OCT image
32 Video image data
321 First video image data
322 Second video image data
33 Pixel
40 Control unit
50 User interface
55 Device interface
60 Virtual viewing direction
601 First virtual viewing direction
602 Second virtual viewing direction
61 Azimuth angle
62 Elevation angle
63 Optical axis of the OCT system
65 Sample
66 Field of view
651 Surface element
652 Volume element
70 Medical instrument

The invention claimed is:

1. A system for acquiring and visualizing optical coherence tomography (OCT) signals, comprising:
an OCT system;
a surgical microscope designed to acquire a time-resolved image signal of a selected field of view of a sample;
a display designed for the time-resolved display of image data; and
a processor configured to drive the OCT system to acquire a time-resolved OCT signal of the selected field of view of the sample and to determine a time-resolved OCT image on the basis of the acquired time-resolved OCT signal and a specifiable virtual viewing direction and to display the time-resolved OCT image on the display,
wherein the processor is further configured to determine corresponding video image data on the basis of the acquired time-resolved image signal and to simultaneously or sequentially display the video image data and the time-resolved OCT image on the display.

2. The system according to claim 1, wherein the virtual viewing direction is defined by an azimuth angle and an elevation angle relative to the optical axis of the OCT system.

3. The system according to claim 1, wherein the processor is configured to determine the time-resolved OCT image as a three-dimensional volume image from the perspective of the virtual viewing direction.

4. The system according to claim 1, wherein the system further comprises a user interface designed to acquire a user input and the virtual viewing direction is determined on the basis of the user input and/or wherein the system further comprises a device connector for connecting the surgical microscope designed for tracking a medical or medical engineering instrument and the virtual viewing direction is determined on the basis of a pose, a position and/or a state of the medical or medical engineering instrument as a device parameter acquired by the device connector.

5. The system according to claim 1, wherein the OCT signal contains a multiplicity of tuples each representing a volume element of the sample and a scattering intensity, wherein the display comprises a multiplicity of pixels and wherein the processor is configured to determine images in such a way on the basis of the tuples, a resolution of the display and the virtual viewing direction that certain pixels correspond to certain volume elements.

6. The system according to claim 1, wherein the processor is configured to sequentially display the video image data and the time-resolved OCT image on the display with the same magnification, the same perspective and/or the same stereo angle $\alpha$.

7. The system according to claim 1, wherein the processor is configured to simultaneously display the video image data with a first level of transparency and the time-resolved OCT image with a second level of transparency on the display.

8. The system according to claim 1,
wherein the display is designed to display stereoscopic images, and
wherein the processor is configured to determine a time-resolved first OCT image and a time-resolved second OCT image on the basis of the time-resolved OCT signal, the virtual viewing direction and a stereo angle $\alpha$, and to stereoscopically display the first OCT image and the second OCT image on the display.

9. The system according to claim 8, wherein the processor is configured to determine the stereo angle $\alpha$ on the basis of a user input acquired by a user interface.

10. The system according to claim 8, wherein the processor is configured to determine the stereo angle a on the basis of optical parameters of the surgical microscope.

11. The system according to claim 10, wherein the surgical microscope comprises a stereo camera with a first stereo lens arranged along a first optical axis and a second stereo lens arranged along a second optical axis and the stereo angle $\alpha$ is an angle between the first optical axis and the second optical axis, and wherein the processor is further designed to determine the stereo angle $\alpha$ on the basis of a zoom level and/or a working distance of the stereo camera.

12. The system according to claim 8, wherein the processor is configured to determine a phase of a performed operation and to determine the stereo angle $\alpha$ on the basis of the phase of the performed operation.

13. The system according to claim 8, further comprising a medical instrument, wherein the processor is configured to determine a position, a type and/or a state of the medical instrument and to determine the stereo angle $\alpha$ and/or the virtual viewing direction on the basis of the position, the type and/or the state of the medical instrument.

14. A method for acquiring and visualizing optical coherence tomography (OCT) signals, including the method steps of:

acquiring a time-resolved OCT signal of a selected field of view of a sample by an OCT system, wherein the OCT signal comprises a multiplicity of tuples each representing a volume element of the sample and a scattering intensity corresponding to the volume element;

determining a given virtual viewing direction;

determining a time-resolved OCT image on the basis of the tuples, a resolution of a display and the virtual viewing direction as a three-dimensional volume image from the perspective of the virtual viewing direction;

acquiring a time-resolved image signal of the selected field of view of the sample via a surgical microscope;

determine corresponding video image data on the basis of the acquired time-resolved image signal; and displaying the time-resolved OCT image on the display and simultaneously or sequentially display the video image data on the display.

15. The method according to claim 14, further including the method steps of:

determining a time-resolved first OCT image and a time-resolved second OCT image in each case on the basis of the tuples, the resolution of the display, the virtual viewing direction and a stereo angle $\alpha$, and in each case as a three-dimensional volume image from the perspective of the virtual viewing direction; and stereoscopically displaying the time-resolved first OCT image and the time-resolved second OCT image on the display.

16. The method according to claim 14, wherein a given virtual viewing direction is determined on the basis of a user input acquired by a user interface and/or on the basis of a device parameter acquired by a device connector.

* * * * *